(12) United States Patent  
Nguyen

(10) Patent No.: US 6,950,025 B1  
(45) Date of Patent: Sep. 27, 2005

(54) MEDICAL SURGERY SAFETY DEVICE

(76) Inventor: Li Nguyen, 14571 Magnolia St., No. 209, Westminster, CA (US) 92683

( * ) Notice: Subject to any disclaimer, the term of this patent is extended or adjusted under 35 U.S.C. 154(b) by 0 days.

(21) Appl. No.: 10/150,630

(22) Filed: May 17, 2002

(51) Int. Cl.$^7$ ............................................ G08B 23/00
(52) U.S. Cl. ......................... 340/573.1; 604/31; 606/42
(58) Field of Search ............................. 340/573.1, 679; 604/31; 606/42

(56) References Cited

U.S. PATENT DOCUMENTS 5,569,188 A * 10/1996 Mackool ...................... 604/67
5,575,789 A * 11/1996 Bell et al. ...................... 606/42
6,332,891 B1 * 12/2001 Himes .......................... 606/169

FOREIGN PATENT DOCUMENTS

JP          11-137673      *  5/1999

* cited by examiner

Primary Examiner—Thomas Mullen
(74) Attorney, Agent, or Firm—Thomas I. Rozsa; Tony D. Chen

(57) ABSTRACT

A medical surgery safety device used in connection with surgical insulting instruments and other operation room medical equipment. The safety device includes one or more remote unit attached to the surgical insulting instruments and the medical equipment and having an accelerometer for detecting a sudden motion of the medical equipment, and a radio frequency signal transmitter for transmitting a radio frequency signal upon detection of such sudden motion. The safety device also includes a base unit attached to a main surgical insulting instrument and having an accelerometer for detecting a sudden motion of the main surgical insulting instrument, and a radio frequency signal receiver for receiving the radio frequency signal from the remote units. The base unit also include a power inlet connected to an external electrical power source and a power outlet for providing electrical power to the surgical insulting instruments. The power to all surgical insulting instruments is interrupted, however, upon either the detection of the sudden motion by the accelerometer of the base unit or the reception of the radio frequency signal from the remote units.

43 Claims, 3 Drawing Sheets

MEDICAL SURGERY SAFETY DEVICE

BACKGROUND OF THE INVENTION

1. Field of the Invention

The present invention generally relates to the field of medical surgical equipment. More particularly, the present invention relates to the field of safety devices for ensuring the safety of medical and dental surgeries and operations.

2. Description of the Prior Art

Modern development and advancement of medical surgical equipment and techniques often require a surgeon to perform a critical medical surgery, operation or procedure with a very high degree of precision under the microscopes or endoscopes. In many cases the surgery, operation or procedure is performed within a very limited and narrow field of operation, often at the millimeter level and does not allow the surgeon any opportunity to pay attention to his surroundings.

However, this high degree precision in a surgical process can be easily interrupted by an unintended, sudden movement of other persons or objects surrounding the surgeon. For example, a patient under light anesthesia may suddenly move or jerk in response to a pain. An anesthesiologist often has to check on the patient's airway or intravenous (IV) injection tube under the drape, which may also cause sudden movement of the patient or the operating table. Nurses or scrub technicians may inadvertently rest on the operating table during a long surgery process. Any operation room personnel may accidently bump the instruments, the surgeon, or the operating table.

All these and many other factors or events (such as an earthquake or other emergency situations) may result in a sudden movement of the patient's body, the surgeon, or the surgical equipment, which can have a devastating consequence because the magnitude of change is amplified significantly at the narrow operating field. Such sudden movement, for example, often causes temporary loss of visual sight under a microscope or endoscope and misalignment of the surgical equipment, which will then transform from an insulting instrument to an insulting weapon. Moreover, many modern surgical procedures now utilize laser, drills, electrocautery, or other insulting instruments which when misaligned or misapplied can cause irreversible injury. Surgical insulting instruments from here on refer to instruments that are used for operating on the patient.

Hence the combination of sudden movement, narrow operating field, and dangerous surgical insulting instruments have created a major hazard in the operation room and posted a real threat to the patient. However, currently there is no simple safety device available to address this problem. It is therefore desirable to provide a medical surgery safety device that can sense the sudden movement of the surroundings in an operation room and upon sensing such a sudden movement immediately cease the function of all surgical insulting instruments, so that no further damage can be done to a patient.

The concept of having an emergency disconnection of power that can be conveniently achieved is also an advantage in cases where the on/off switch location is difficult to reach or the on/off switch of the insulting instruments may malfunction. This concept can be applied to other dangerous machines in other fields such as meat cutting machine, table saw, or printing machine . . . etc. There are other applications for this product besides being used in the OR, including:

1. Monitoring an object or a person's movement to set off an alarm for security reasons.
2. If engineering is sophisticated enough with this device, one also track not only the movement of an object or person but also the direction and distance in which they are moving. This information is useful but has its limitations.
3. There can be a tilt mechanism attached to or built into various machines or games where rough movements by the operator is discouraged.

SUMMARY OF THE INVENTION

The present invention is a novel and unique medical surgery safety device. It is a motion analysis injury limited immolator (M.A.I.L.I.).

The primary object of the present invention is to provide a medical surgery safety device that can detect the sudden movement of the objects surrounding a surgeon performing a medical surgery on a patient, and upon detecting such a sudden movement immediately cut off power to the surgical instrument so that no further injury can be inflicted on the patient.

The present invention medical surgery safety device includes a base unit and several remote units. The base unit is plugged into a wall outlet, and has many subsequent outlets into which all insulting instruments will be plugged. The main surgical insulting instrument such as a laser is then plugged into the base unit and gets its power through the base unit. The base unit is attached to the main insulting instrument and has a motion-sensing mechanism that will emit an audible and visual alarm and cut off the power to the main insulting instrument when it detects a sudden force or motion beyond a certain pre-determined range. The base unit also has a reset button to reset the unit once the situation is stabilized.

The remote units of the present invention medical surgery safety device are battery operated. These remote units may be attached to the operating table, the patient, other insulting instruments, or other surrounding equipment which may directly or indirectly affect the stability or the precision of the main surgical insulting instrument. When the remote unit detects a movement, it will also emit an audible and visual alarm. Moreover, it will send a radio frequency signal to the base unit to cause it immediately to shut off the power to all of the surgical insulting instruments. The audible and visual alarm can help the surgeon to determine where is the source of the sudden movement and whether anything needs to be realigned or recalibrated.

This unit also has an on/off switch and a bypass switch to allow continuation of surgery and motion sensing, when the remote units malfunction or in cases where the OR equipment suddenly develops vibrations or motions that are steadied and do not appear to interfere with surgery.

The main novel features and advantages of the present invention medical surgery safety device are that it provides a motion-sensing device that will automatically turn off all surgical insulting instruments, i.e. the laser or the drill or electrocautery, when it detects sudden movements. In addition, the remote units are battery operated and communicate by radio frequencies with the base unit so that they can be placed anywhere as needed without having wires running all over the operation room. Furthermore, both the base unit and the remote units are compact and light weight, and can be easily moved from one instrument to another instrument, or from one operation room to another operation room. They can also be placed in any position, not necessarily parallel to the ground like all other tilt mechanisms. Another advantage is that just the presence of the device itself will encourage more alertness and careful movement of OR personnel by acting like a warning sign.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
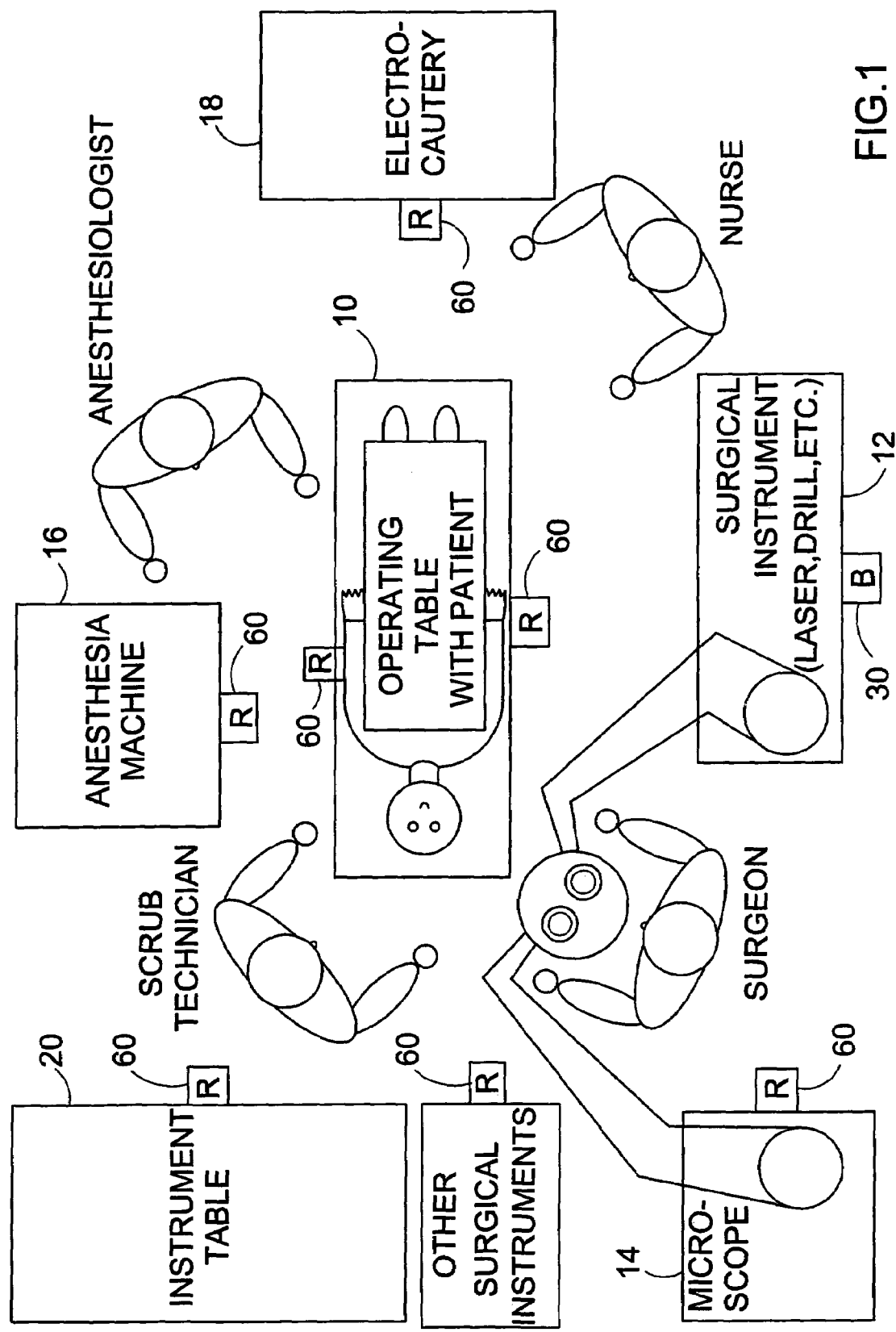
FIG. 1 is an over-head view illustrating the placement and arrangement of the present invention medical surgery safety device in an operation room environment.

Referring to FIG. 1, there is shown a typical medical surgery operation room (OR) environment. The medical professionals in the OR often include a surgeon, one or more nurses, scrub technicians and anesthesiologists. The medical equipment in the OR often includes an operating table 10 for carrying a patient undergoing the surgery, a main surgical insulting instrument 12 and other surgical instruments, such as a laser, a microscope (or endoscope) 14, an anesthesiology machine 16, an electrocautery 18 and an instrument table 20.

Typically, the surgeon performs the surgery with the surgical insulting instrument 12 under the microscope (or endoscope) 14, the anesthesiologist operates an anesthesia machine 16, and the nurse and the scrub technician work near the electro-cautery 18 and the instrument table 20, respectively, in assistance to the surgeon. Of course there may be other medical professionals and medical equipment in the OR depending on the need or particular type of surgery procedure.

The present invention medical surgery safety device includes a base unit 30 and several remote units 60. The internal structural and functional components of the base unit 30 and remote units 60 will be described in detail below. However, the basic set-up and functional features of the base unit 30 and remote units 60 are as follows.

The base unit 30 is connected to an alternating current (AC) power source such as a wall outlet; however it can be battery powered. It does not need to be AC powered to control an AC device. The electricity power cords of the surgical insulting instruments 12 are plugged into the base unit 30 and draw AC power through the base unit 30. The base unit has a motion-sensing mechanism that will emit an auditory signal as well as a visible signal and cut off the AC power to all surgical insulting instruments 12 when it detects a sudden impact or motion of the main surgical insulting instrument. The base unit can turn "off" any insulting devices by switching "off" the switch of the base unit.

The remote units 60 are respectively attached to the patient, the operating table 10, the microscope 14, the anesthesia machine 16, the electro-cautery 18, the instrument table 20, and any other medical instruments or devices in the OR that may affect the safe and precise operation of the surgical instruments upon a sudden impact or motion. When any one of the remote units 60 detects a movement, it will send a radio frequency signal to the base unit 30, which in turn will immediately shut off the AC power to all of the surgical insulting instruments 12 so that no further harm can be done until the situation stabilizes.

Figure 2:
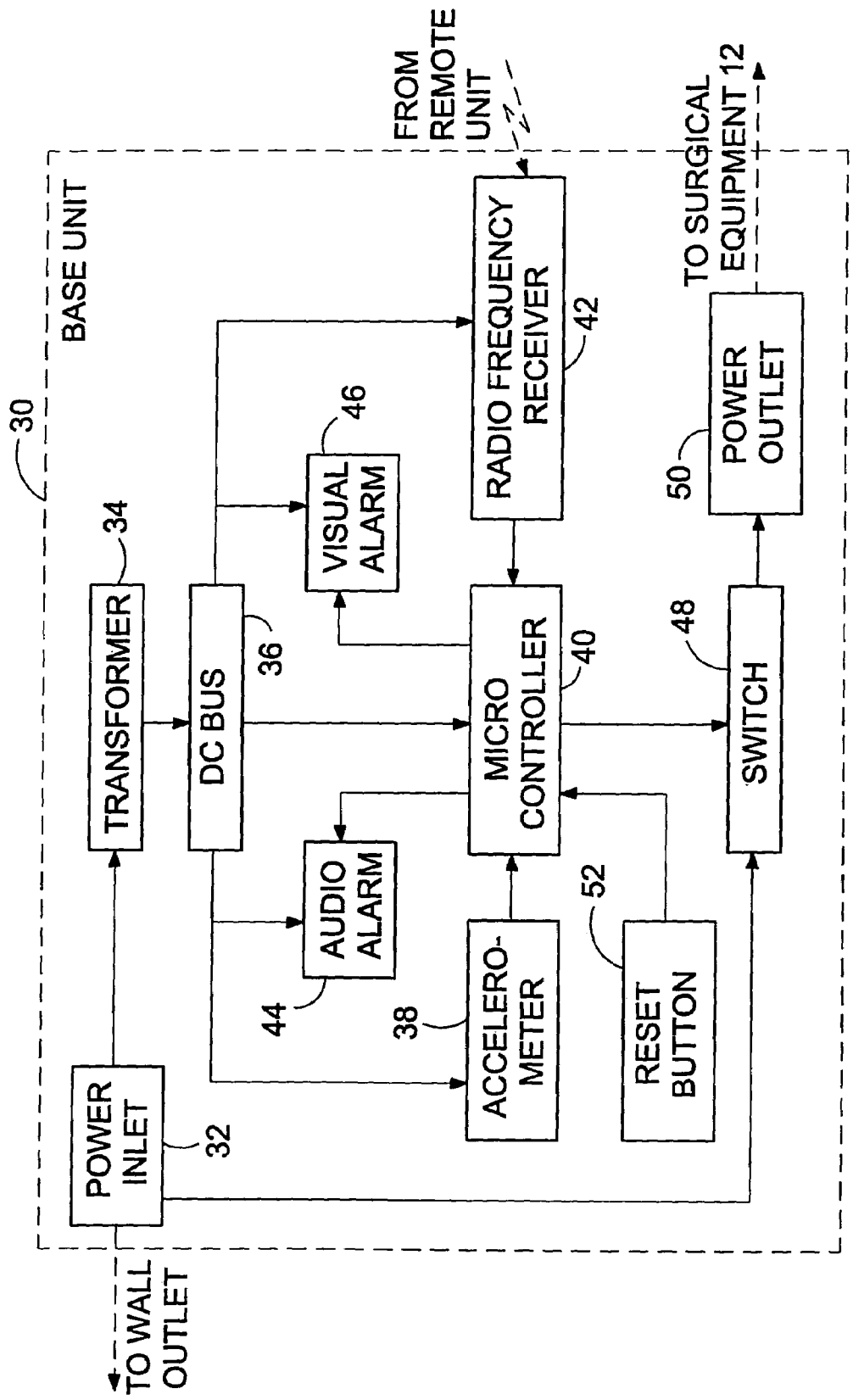
FIG. 2 is a block diagram showing the main functional components of the base unit of the present invention medical surgery safety device.

Referring to FIG. 2, there is shown the main structural and functional components of the base unit 30 of the present invention medical surgery safety device. The base unit 30 has a power inlet 32 for connection to an external AC power source such as an uninterrupted power supply (UPS), a power strip or an ordinary wall outlet.

The AC power obtained from the power inlet 32 is transformed into direct current (DC) power by a transformer 34. The output of the transformer 34 is connected to a DC bus 36 of the base unit 30. The DC bus 36 supplies DC power to other DC components of the base unit 30, including an accelerometer 38, a micro controller 40, a radio frequency receiver 42, an audio alarm 44 and a visual alarm 46.

The accelerometer 38 is used to detect a sudden impact or motion upon the base unit 30. This may happen when someone inadvertently or accidentally bumped the main surgical insulting instrument. The accelerometer is not a constant motion sensor. Rather, it detects the acceleration, i.e., the rate of change of the velocity, of its internal meter, and it can be mounted in any orientation and there is no requirement that it has to be leveled as other types of motion sensors. The accelerometer 38 can have an adjustable pre-determined level, only above which a triggering signal will be generated and sent out.

The accelerometer can have its sensitivity adjusted to detect any motion even if it is slow and smooth, because all motion must have acceleration and deceleration. The accelerometer can also measure tilt from the initial placement of the device and combinations of motion and tilt. Both the base and remote units can have a multiplicity of sensors as well, and can include sensors that not only measure motion, but other things such as sound (to sense things such as motor failures or dropping glass), fluids (to sense leaks), or gases (to prevent explosions or poisonings).

Upon detecting a sudden impact or motion above the pre-determined level, the accelerometer 38 will send a signal to the micro controller 40, which will in turn perform a series of functions. The micro controller 40 will send a signal to the audio alarm 44 which will in turn generate an audible alarm. The micro controller 40 will also send a signal to the visual alarm 46 which will in turn generate a visible alarm. The audible alarm and visible alarm are designed to alert the surgeon and other medical professionals in the OR of the origin of the sudden impact or motion.

More importantly, the micro controller 40 will operate and change the status of a switch 48 which is connected between the AC power inlet 32 and an AC power outlet 50 of the base unit 30, from which the surgical instrument 12 (shown in FIG. 1) draws electrical power, to cut off immediately any AC power to the surgical insulting instrument 12 so that the main surgical insulting instrument and all other insulting instruments 12 cease to operate and are incapable of causing any further injury or damage to the patient as a result of the sudden impact.

Under normal circumstances, the status of the switch 48 is closed which allows AC power to flow from the power inlet 32 to power outlet 50 of the base unit 30, such that all surgical insulting instruments 12 can draw electrical power therefrom and function normally. However, when triggered by a sudden impact or motion, the status of the switch 48 is changed from closed to open by the micro controller 40 which prevents AC power from flowing to power outlet 50 such that all surgical insulting instruments 12 will be stopped.

The means of receiving signals from the remote units is via RF signals. However, the use of wires (such as in twisted pair or plug-in networking), or infrared emitters/detectors can be used.

The radio frequency receiver 42 of the base unit 30 is used for receiving wireless radio frequency signals from the remote units 60 upon the detecting of a sudden impact by one or more of the remote units 60. The radio frequency receiver 42 will then send a signal to the micro controller 40, which will in turn perform the series of functions described earlier, just as when it receives a signal from the accelerometer 38. Each remote unit has its own unique address so that the base unit knows what remote unit has been triggered. The remote unit can also be switched to send out alarms only instead of turning off the insulting instrument. The base unit station also timestamps time/date/remote unit event times. Because each remote unit sends out its address, the base unit can be programmed to only listen for specific remote units, to filter out any transmissions from another room or area.

The base unit 30 has a reset button 52 which can be pressed once the situation is stabilized to cause the micro controller 40 to reset the base unit 30 so it returns to its normal status and ready to detect the next sudden motion.

Figure 3:
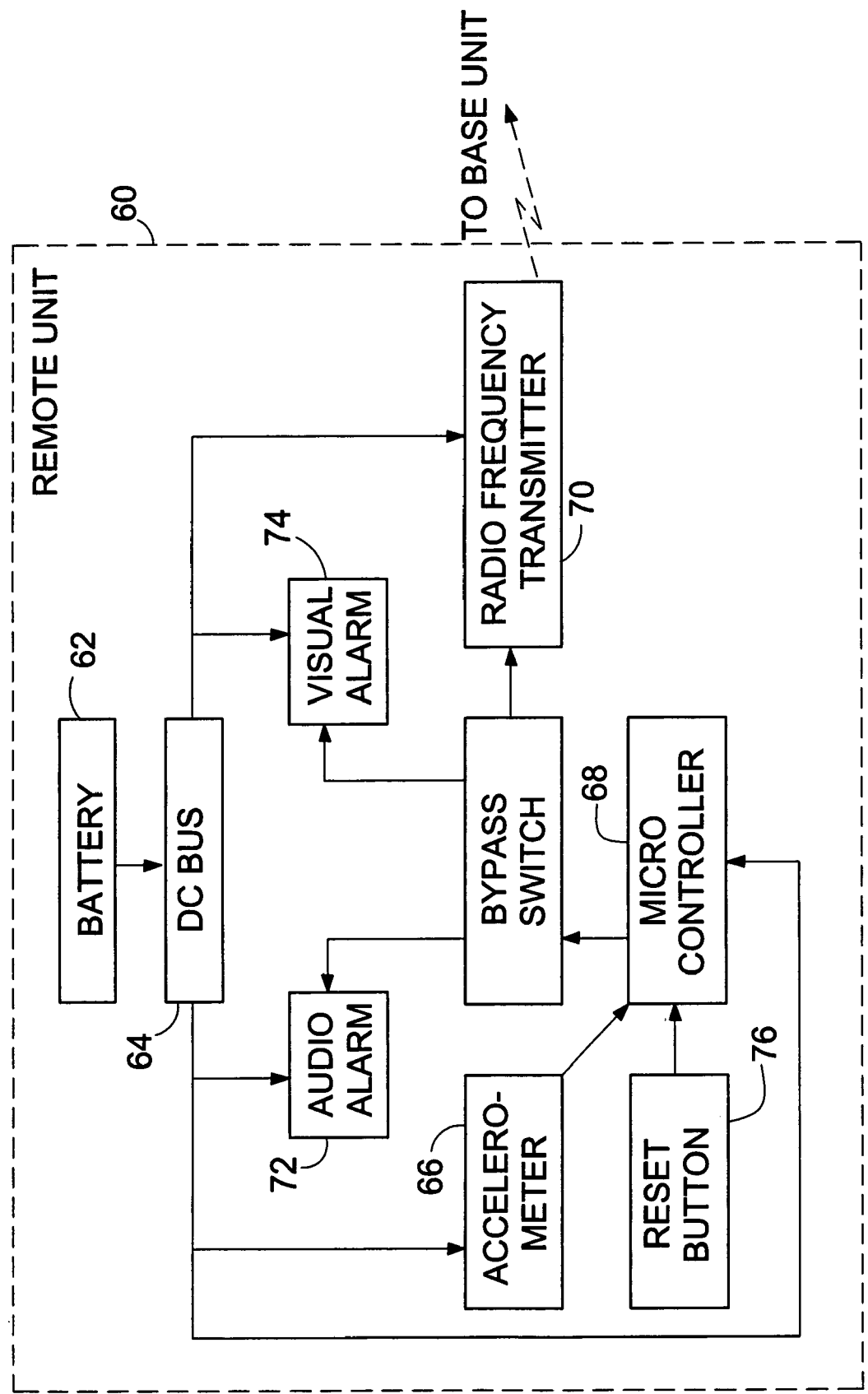
FIG. 3 is a block diagram showing the main functional components of a remote unit of the present invention medical surgery safety device.

Referring to FIG. 3, there is shown the main structural and functional components of one of the remote units 60 of the present invention medical surgery safety device. The remote unit 60 has a battery pack 62 for providing DC power to a DC bus 64 of the remote unit 60. The DC bus 64 supplies DC power to other DC components of the remote unit 60, including an accelerometer 66, a micro controller 68, a radio frequency transmitter 70, an audio alarm 72 and a visual alarm 74.

Again, the accelerometer 66 is used to detect a sudden impact or motion upon the remote unit 60. The accelerometer 66 has an adjustable pre-determined level, only above which a triggering signal will be generated and sent out. Upon detecting a sudden impact or motion above the pre-determined level, the accelerometer 66 will send a signal to the micro controller 68, which will in turn perform a series of functions. The micro controller 68 will send a signal to the audio alarm 72 which will in turn generate an audible alarm. The micro controller 68 will also send a signal to the visual alarm 74 which will in turn generates a visible alarm. The audible alarm and visible alarm are designed to alert the surgeon and other medical professionals in the OR of the origin of the sudden impact or motion.

Moreover, the micro controller 68 of the remote unit 60 will cause the radio frequency transmitter 70 to send a wireless radio frequency signal to the radio frequency receiver 42 of the base unit 30, so that the micro-controller 40 of the base unit 30 can operate and change the status of a switch 48 to cut off immediately any AC power to the main surgical insulting instrument 12 so that the surgical insulting instrument 12 stops operating and is prevented from any further operation until the situation is stabilized and the safety device is reset.

The remote unit 60 also has a reset button 76 which can be pressed once the situation is stabilized to cause the micro controller 68 to reset the remote unit 60 so it returns to its normal status and ready to detect the next sudden motion. The remote unit also has a bypass switch that allows it to continue to monitor and record motion but does not activate the alarm or radio frequency transmitter, thus allowing the surgery to continue.

For safety considerations, the medical surgery safety device of the present invention is arranged in such a fashion that it will only shut off the surgical instrument, but not other medical equipment in the OR. All other medical equipment, such as the anesthesia machine, remain operational.

The present invention has many novel and unique features and advantages. It provides a sudden motion detection or sensing device that will automatically turn off all surgical insulting instruments such as a laser or drill or electrocautery, when a sudden movement in the patient, the OR bed, the surgical instrument or other medical equipment in the OR occurs. The remote units are operated on battery power and communicate with the base unit through wireless radio frequency transmission so that they can be placed anywhere as needed without having wires lying around all over the OR. The base and the remote units are designed and constructed as compact and light weight, and can be easily attached to the patient or any medical equipment, or be moved from one instrument to another, or from one OR to another, in a very short time period. Moreover, the base and remote units can be produced as stand-alone devices, retrofitted into existing medical instruments and equipment, or incorporated into new medical instruments and equipment. Finally, the base unit can function by itself without any remote units.

Defined in detail, the present invention is a medical surgery safety device used in connection with a surgical instrument and other operation room medical equipment, comprising: (a) a base unit attached to the main surgical insulting instrument such as a laser and having a power inlet for connecting to an external electrical power source, a power outlet for providing electrical power to the main surgical insulting instrument and others such as drill and electrocautery, and a switch connected between the power inlet and outlet, where the switch is normally closed to allow electrical power to pass from the power inlet to the power outlet for ordinary operation of the surgical insulting instrument; (b) the base unit also having an accelerometer for detecting a sudden motion of the main surgical insulting instrument; (c) a multiplicity of remote units each attached to a respective piece of the medical equipment and having an accelerometer for detecting a sudden motion of the respective piece of the medical equipment; (d) each remote unit also having means for transmitting a wireless radio frequency signal upon detection of the sudden motion of the respective piece of the medical equipment; (e) the base unit further having means for receiving the wireless radio frequency signal; and (f) the base unit additionally having means for causing the switch to open upon either the detection of the sudden motion by the accelerometer of the base unit or the reception of the wireless radio frequency signal; (g) whereby when a sudden motion of the surgical insulting instrument or any piece of the medical equipment is detected, the electrical power to all surgical insulting instruments will be cut-off immediately to prevent any further operation of all surgical insulting instruments.

Defined broadly, the present invention is a medical surgery safety device used in connection with a surgical instrument and other operation room medical equipment, comprising: (a) at least one remote unit attached to a piece of medical equipment and having an accelerometer for detecting a sudden motion of the medical equipment, and means for transmitting a radio frequency signal upon detection of such sudden motion; (b) a base unit attached to the main surgical insulting instrument and having an accelerometer for detecting a sudden motion of the main surgical insulting instrument, and means for receiving the radio frequency signal; and (c) a base unit having means connected to an external electrical power source for providing electrical power to all of the surgical insulting instruments, which can be interrupted upon either the detection of the sudden motion by the accelerometer of the base unit or the reception of the radio frequency signal from the at least one remote unit; (d) whereby when a sudden motion of the surgical instrument or the medical equipment is detected, the electrical power to all surgical insulting instruments will be cut-off immediately to prevent any further operation of all surgical insulting instruments.

Defined more broadly, the present invention is a medical surgery safety device used in connection with a surgical insulting instrument, comprising: (a) a base unit attached to the main surgical insulting instrument and having means connected to an external electrical power source for providing electrical power to this and other surgical insulting instrument; and (b) the base unit having means for detecting a sudden motion of the surgical instrument and preventing the electrical power from being provided to the surgical instrument upon the detection of the sudden motion.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A medical surgery safety device used in connection with surgical insulting instruments and other operation room medical equipment, comprising:
   a. a base unit attached to one of said surgical insulting instruments and having a power inlet for connecting to an external electrical power source, a power outlet for providing electrical power to said surgical insulting instruments, and a switch connected between the power inlet and outlet, where the switch is normally closed to allow electrical power to pass from the power inlet to the power outlet for ordinary operation of said surgical insulting instruments;
   b. said base unit also having an accelerometer for detecting a sudden motion of said one of said surgical insulting instruments;
   c. a multiplicity of remote units each attached to a respective one of other said surgical insulting instruments and said medical equipment and having an accelerometer for detecting a sudden motion of said respective one of said other surgical insulting instruments and said medical equipment;
   d. each said remote unit also having means for transmitting a wireless radio frequency signal upon detection of said sudden motion;
   e. said base unit further having means for receiving said wireless radio frequency signal; and
   f. said base unit additionally having means for causing said switch to open upon either the detection of said sudden motion by said accelerometer of said base unit or the reception of said wireless radio frequency signal;
   g. whereby when a sudden motion of said surgical insulting instruments or said medical equipment is detected, said electrical power to said surgical insulting instruments will be cut-off immediately to prevent any further operation of said surgical insulting instruments.

2. The device in accordance with claim 1, wherein said means of each said remote unit for transmitting wireless radio frequency signal is a radio signal transmitter.

3. The device in accordance with claim 1, wherein said means of said base unit for receiving wireless radio frequency signal is a radio signal receiver.

4. The device in accordance with claim 1, wherein said means of said base unit for causing said switch to open is a micro-controller.

5. The device in accordance with claim 1, wherein said base unit further comprises a transformer connected to said power inlet for providing internal electrical power to said base unit.

6. The device in accordance with claim 1, wherein said base unit further comprises an audio alarm for providing an audible signal when said accelerometer of said base unit detects a sudden motion.

7. The device in accordance with claim 1, wherein said base unit further comprises a visual alarm for providing a visual signal when said accelerometer of said base unit detects a sudden motion.

8. The device in accordance with claim 1, wherein said base unit further comprises a reset button for resetting said base unit.

9. The device in accordance with claim 1, wherein each said remote unit is powered by an internal battery pack.

10. The device in accordance with claim 1, wherein each said remote unit further comprises a micro-controller for causing said radio frequency transmitting means to transmit a radio signal when said accelerometer of said remote unit detects a sudden motion.

11. The device in accordance with claim 1, wherein each said remote unit further comprises an audio alarm for providing an audible signal when said accelerometer of said remote unit detects a sudden motion.

12. The device in accordance with claim 1, wherein each said remote unit further comprises a visual alarm for providing a visual signal when said accelerometer of said remote unit detects a sudden motion.

13. The device in accordance with claim 1, wherein said remote unit further comprises a reset button for resetting said remote unit, and also a bypass button to allow for continuation of motion monitoring without activation of audio or visual alarm and radio frequency transmitter of said remote unit.

14. A medical surgery safety device used in connection with a surgical instrument and other operation room medical equipment, comprising:
   a. at least one remote unit attached to a piece of medical equipment and having an accelerometer for detecting a sudden motion of the medical equipment, and means for transmitting a radio frequency signal upon detection of such sudden motion;
   b. a base unit attached to a surgical instrument and having an accelerometer for detecting a sudden motion of the surgical instrument, and means for receiving said radio frequency signal; and
   c. said base unit having means connected to an external electrical power source for providing electrical power to said surgical instrument, which can be interrupted upon either the detection of said sudden motion by said accelerometer of said base unit or the reception of said radio frequency signal from said at least one remote unit;
   d. whereby when a sudden motion of said surgical instrument or said medical equipment is detected, said electrical power to said surgical instrument will be cut-off immediately to prevent any further operation of said surgical instrument.

15. The device in accordance with claim 14, wherein said means of said base unit connected to said external electrical power source for providing electrical power to said surgical instrument comprises a power inlet to be connected to said external electrical power source.

16. The device in accordance with claim 14, wherein said means of said base unit connected to said external electrical power source for providing electrical power to said surgical instrument comprises a power outlet for connection with said surgical instrument.

17. The device in accordance with claim 14, wherein said means of said at least one remote unit for transmitting radio frequency signal is a radio signal transmitter.

18. The device in accordance with claim 14, wherein said means of said base unit for receiving radio frequency signal transmitted by said at least one remote unit is a radio signal receiver.

19. The device in accordance with claim 14, wherein said base unit further comprises a transformer for providing internal electrical power to said base unit.

20. The device in accordance with claim 14, wherein said base unit further comprises an audio alarm for providing an audible signal when said accelerometer of said base unit detects a sudden motion.

21. The device in accordance with claim 14, wherein said base unit further comprises a visual alarm for providing a visual signal when said accelerometer of said base unit detects a sudden motion.

22. The device in accordance with claim 14, wherein said base unit further comprises a reset button for resetting said base unit.

23. The device in accordance with claim 14, wherein said at least one remote unit is powered by an internal battery pack.

24. The device in accordance with claim 14, wherein said at least one remote unit further comprises an audio alarm for providing an audible signal when said accelerometer of said remote unit detects a sudden motion.

25. The device in accordance with claim 14, wherein each said at least one remote unit further comprises a visual alarm for providing a visual signal when said accelerometer of said remote unit detects a sudden motion.

26. The device in accordance with claim 14, wherein said at least one remote unit further comprises a reset button for resetting said at least one remote unit, and also a bypass button to allow for continuation of motion monitoring without activation of audio or visual alarm and radio frequency transmitter of said remote unit.

27. A medical surgery safety device used in connection with a surgical instrument, comprising:
   a. a base unit attached to said surgical instrument and having means connected to an external electrical power source for providing electrical power to said surgical instrument; and
   b. said base unit having means for detecting a sudden motion of said surgical instrument and preventing said electrical power from being provided to said surgical instrument upon the detection of said sudden motion.

28. The device in accordance with claim 27, wherein said means of said base unit connected to said external electrical power source for providing electrical power to said surgical instrument comprises a power inlet to be connected to said external electrical power source.

29. The device in accordance with claim 27, wherein said means of said base unit connected to said external electrical power source for providing electrical power to said surgical instrument comprises a power outlet for connection with said surgical instrument.

30. The device in accordance with claim 27, wherein said detecting means of said base unit is an accelerometer.

31. The device in accordance with claim 27, wherein said base unit further comprises a transformer for providing internal electrical power to said base unit.

32. The device in accordance with claim 27, wherein said base unit further comprises an audio alarm for providing an audible signal upon detection of a sudden motion.

33. The device in accordance with claim 27, wherein said base unit further comprises a visual alarm for providing a visual signal upon detection of a sudden motion.

34. The device in accordance with claim 27, wherein said base unit further comprises a reset button for resetting said base unit.

35. The device in accordance with claim 27, further comprising at least one remote unit attached to a medical equipment and having means for detecting a sudden motion of said medical equipment, and means for transmitting a radio frequency signal upon detection of such sudden motion.

36. The device in accordance with claim 35, wherein said means of said at least one remote unit for transmitting radio frequency signal is a radio signal transmitter.

37. The device in accordance with claim 35, wherein said base unit further comprises means for receiving radio frequency signal transmitted by said at least one remote unit to prevent said electrical power from being provided to said surgical instrument upon reception of said radio signal.

38. The device in accordance with claim 37, wherein said means of said base unit for receiving radio frequency signal transmitted by said at least one remote unit is a radio signal receiver.

39. The device in accordance with claim 35, wherein said at least one remote unit is powered by an internal battery pack.

40. The device in accordance with claim 35, wherein said at least one remote unit further comprises an audio alarm for providing an audible signal when said accelerometer of said remote unit detects a sudden motion.

41. The device in accordance with claim 35, wherein each said at least one remote unit further comprises a visual alarm for providing a visual signal when said accelerometer of said remote unit detects a sudden motion.

42. The device in accordance with claim 35, wherein said at least one remote unit further comprises a reset button for resetting said at least one remote unit.

43. The device in accordance with claim 35, wherein said at least one remote unit further comprises a bypass button to allow continuation of motion monitoring without activation of audio or visual alarm and radio frequency transmitter of said at least one remote unit.

* * * * *